US006858575B2

(12) United States Patent
Smets et al.

(10) Patent No.: US 6,858,575 B2
(45) Date of Patent: Feb. 22, 2005

(54) PRO-PERFUME COMPOSITIONS AND SUBSTRATE-TREATING PRODUCTS AND METHODS USING THEM

(75) Inventors: Johan Smets, Lubbeek (BE); Rafael Trujillo, Mason, OH (US); Christophe Laudamiel, New York, NY (US)

(73) Assignee: Procter & Gamble Company, Cincinnati, OH (US)

( * ) Notice: Subject to any disclaimer, the term of this patent is extended or adjusted under 35 U.S.C. 154(b) by 201 days.

(21) Appl. No.: 10/304,937

(22) Filed: Nov. 26, 2002

(65) Prior Publication Data

US 2003/0171250 A1 Sep. 11, 2003

(51) Int. Cl.$^7$ .................................................. A61K 7/46

(52) U.S. Cl. ............................... 512/2; 512/1; 510/101; 510/102

(58) Field of Search ......................... 512/1, 2; 510/101, 510/102

(56) References Cited

U.S. PATENT DOCUMENTS 5,482,649 A 1/1996 Meixner et al.

FOREIGN PATENT DOCUMENTS

| | | | |
|---|---|---|---|
| EP | 280 222 | A2 | 9/1988 |
| EP | 1 116 788 | A1 | 7/2001 |
| WO | WO 99/15580 | A1 | 4/1999 |
| WO | WO 00/02981 | A2 | 1/2000 |
| WO | WO 00/02982 | A2 | 1/2000 |
| WO | WO 00/02987 | A2 | 1/2000 |
| WO | WO 00/02991 | A1 | 1/2000 |

*Primary Examiner*—Monique T. Cole

(74) *Attorney, Agent, or Firm*—Armina E. Matthews; Kim W. Zerby; Steve W. Miller

(57) ABSTRACT

Disclosed herein are pro-perfume compositions comprising the Michael Addition reaction product of a primary and/or secondary amine compound with an unsaturated ester, acid or nitrile perfume compound. Pro-perfumes made from this selected type of reaction product provide a desirable and prolonged odor benefit to surfaces, e.g., fabrics and hard surfaces, contacted therewith. Such pro-perfumes are also utilized in a wide variety of substrate-treating products and methods.

19 Claims, No Drawings

PRO-PERFUME COMPOSITIONS AND SUBSTRATE-TREATING PRODUCTS AND METHODS USING THEM

CROSS REFERENCE TO RELATED APPLICATIONS

This application claims priority under 35 U.S.C. § 119(a) to European Application Serial No. 01870261.3, filed Nov. 27, 2001.

TECHNICAL FIELD

The present invention relates to pro-perfume compositions, in particular for use in cleaning or fabric treatment products. Such pro-perfume compositions impart sustained release of a beneficial perfume odor profile, i.e., a freshness benefit, on surfaces like fabrics, in particular dry fabrics, which have been treated with such products.

BACKGROUND OF THE INVENTION

Perfumed products are well-known in the art. However, consumer acceptance of such perfumed products like laundry and cleaning products is determined not only by the performance achieved with these products but also by the aesthetics associated therewith. The perfume components are therefore an important aspect of the successful formulation of such commercial products.

It is also desired by consumers for treated surfaces like fabrics to maintain over time the pleasing fragrance imparted by treatment products. Indeed, perfume additives make such compositions more aesthetically pleasing to the consumer, and in some cases the perfume imparts a pleasant fragrance to surfaces, like fabrics, treated therewith. However, the amount of perfume carried-over from an aqueous laundry or cleaning bath onto fabrics is often marginal and does not last long on the surface of the fabrics. Furthermore, fragrance materials are often very costly and their inefficient use in laundry and cleaning compositions and ineffective delivery to surfaces like fabrics results in a very high cost to both consumers and laundry and cleaning manufacturers. Industry, therefore, continues to look with urgency for more efficient and effective fragrance delivery in laundry and cleaning products, especially for improvement in the provision of long-lasting fragrance to treated substrates like fabrics.

Recently, new classes of materials, namely the amine reaction product of a compound containing a primary and/or secondary amine functional group and an active ketone or aldehyde containing perfume component, have found increasing use in the domestic treatment of fabrics in order to provide long lasting perfume release on laundered fabrics. Disclosure of such compounds can be found, for example, in PCT Patent Application Nos. WO 00/02991; WO 00/02981; WO 00/02987 and WO 00/02982.

However, notwithstanding the advances in the art, there is still a need for identifying pro-perfumes which deliver the benefit of a long-lasting fragrance, preferably with a multi-odor profile, to substrates and surfaces treated therewith. There is also still a need to provide pro-perfumes which can be incorporated into a wide variety of substrate-treating products such as cleaning and fabric treatment products.

Accordingly, it is an object of the present invention to provide pro-perfume compositions which can impart a long-lasting beneficial odor profile to surfaces such as fabrics which have been contacted with such pro-perfumes It is a further object of the present invention to provide pro-perfume compositions which can be effectively and stably incorporated into cleaning and other types of fabric or substrate-treatment compositions.

SUMMARY OF THE INVENTION

The present invention provides pro-perfume compositions which can be incorporated into cleaning or substrate-treating products, e.g., detergent compositions, or fabric treatment products. Such pro-perfume compositions comprise the reaction product of a primary and/or secondary amine compound with one or more unsaturated ester, acid and/or nitrile perfume compounds.

The amine compound is one which when reacted with the ester, acid or nitrile perfume compound will yield a Michael Addition reaction product which is in the form of a relatively viscous fluid having a viscosity ranging from about 500 to 100,000,000 centipoise. Preferably the amine compund will be one which has an Odor Intensity Index of less than that of a 1% solution of methylanthranilate in dipropylene glycol.

The selected perfume compounds, which are reacted with the amine compound to form the pro-perfumes herein, are those of the general formula:

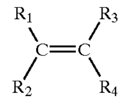

wherein $R_1$ is CN, COOH or COOR, with R being an organic moiety containing no aldehyde or ketone functionalities; and $R_2$, $R_3$ and $R_4$ are each independently H or organic moieties which, together with $R_1$, render the resulting compound a material having perfume characteristics and which permit the resulting compound to undergo a Michael addition reaction with the amine compound. Preferably $R_1$ is COOR with R being a $C_{1-20}$ organic moiety; $R_2$ and $R_3$ are each independently H or $C_{1-4}$ lower alkyl with at least one of $R_2$ or $R_3$ being H, and $R_4$ is H or a $C_{1-20}$ organic moiety. The most preferred compounds of this type are ester perfume compounds having an unsaturated double bond in conjugation with the carbonyl function of the ester group.

The cleaning and substrate treatment products of this invention are those which contain pro-perfume compositions of the foregoing type. Such products impart a sustained, and preferably multi-odor, perfume or freshness benefit to the surfaces treated with such products. Such compositions will generally contain from about 1% to 50% by weight of a cleaning or substrate treating agent such as a detersive surfactant or fabric softening agent. Such compositions will also contain from about 0.005% to 5% by weight of the pro-perfume reaction products hereinbefore described.

In its method aspects, the present invention relates to a method for treating substrates such as fabrics or hard surfaces to impart thereto substantive, slow fragrance release perfume materials. Such a method comprises contacting the substrate (e.g., fabric or other surface) to be treated with an aqueous solution containing from about 0.01 % to 1% by weight of a pro-perfume reaction product as hereinbefore described. The substrate is thereafter dried in such a manner that the pro-perfume reaction product is left deposited on the substrate. The deposited reaction product thereafter releases its weakly chemically bound perfume component slowly over time, thereby imparting sustained fragrance releasing characteristics to the substrate surface.

DETAILED DESCRIPTION OF THE INVENTION

The essential components of the pro-perfume reaction product compositions herein are the primary and/or secondary amine compounds and the unsaturated ester, acid or nitrile perfume compounds which form Michael Addition reaction products with such amines. Each of these components, as well as pro-perfume composition preparation, the substrate treatment products containing such pro-perfume compositions, and methods of treating substrates with the pro-perfume compositions herein are described in detail as follows:

Amine Compound

The amine compound used to form the pro-perfume compostions herein is a primary and/or secondary amine. The term "primary and/or secondary amine", means for purposes of this invention a component which carries at least one primary and/or secondary amine and/or amide function. Of course, one amine compound may carry both primary and secondary amine moieties, thereby enabling a reaction with several unsaturated perfume compounds.

The primary amine and/or secondary amine compounds useful herein are those which are relatively high in molecular weight so that they can impart certain viscosity characterisritcs to the products which result from their reaction with the unsaturated perfume compounds. Thus the amines which are selected are those which ultimately provide a reaction product having a viscosity of from about 500 to 100,000,000 centipoise. More preferably, the amines utilized herein are those which provide a reaction product having a viscosity of from about 5,000 to 15,000,000 centipoise.

The primary amine and/or secondary amine compounds used in this invention are preferably ones which do not themselves contribute any odor or fragrance characteristics to the resulting pro-perfume reaction products which are formed from such amines. Thus the primary and/or secondary amines preferred for use herein are generally ones characterized by having an Odor Intensity Index of less than that of a 1% solution of methylanthranilate in dipropylene glycol.

Odor Intensity Index Method

Odor Intensity Index is a value determined by expert graders who evaluate test chemicals for odor when such the pure chemicals are diluted at 1% in dipropylene glycol (DPG), an odor-free solvent used in perfumery. This concentration percentage is representative of typical usage levels. Smelling strips, or so called "blotters," are dipped in test solutions and presented to the expert panellist for evaluation. Expert panellists are assessors trained for at least six months in odor grading and whose gradings are checked for accuracy and reproducibility versus a reference on an on-going basis. For each amine compound, a panellist is presented two blotters: one reference (Me Anthranilate, unknown from the panellist) and the test sample. The panellist is asked to rank both smelling strips on the 0–5 odor intensity scale, 0 being no odor detected, 5 being very strong odor present.

Results:

The following represents Odor Intensity Index of some amine compounds suitable for use in the present invention and according to the above procedure. In each case, numbers are arithmetic averages among 5 expert panellists and the results are statistically significantly different at 95% confidence level:

| | |
|---|---|
| Methylanthranilate 1% (reference) | 3.4 |
| Ethyl-4-aminobenzoate (EAB) 1% | 0.9 |
| 1,4-bis-(3-aminopropyl)-piperazine (BNPP) 1% | 1.0 |

A wide variety of preferred primary and/or seconday amine compounds which have the requisite Odor Intensity Index characteristics can be used to prepare the pro-perfume compositions of this invention. A general structure for a primary amine compound useful in this invention is as follows:

B—$(NH2)_n$;

wherein B is a carrier material, and n is an index of value of at least 1. Compounds containing a secondary amine group have a structure similar to the above excepted that the compound comprises one or more —NH— groups instead of —NH2. Further, the compound structure may also have one or more of both —NH2 and —NH— groups. Typically the amine compounds of this general type are themselves relatively viscous materials as are the pro-perfume reaction products made therefrom.

Suitable B carriers include both inorganic and organic carrier moieties. By "inorganic carrier", it is meant a carrier which is comprised of non- or substantially non-carbon based backbones.

Preferred primary and/or secondary amines, utilizing inorganic carriers, are those selected from mono or polymers or organic-organosilicon copolymers of amino derivatised organo silane, siloxane, silazane, alumane, aluminum siloxane, or aluminum silicate compounds. Typical examples of such carriers are: organosiloxanes with at least one primary amine moiety like the diaminoalkylsiloxane [H2NCH2(CH3)2Si]O, or the organoaminosilane (C6H5) 3SiNH2 described in: Chemistry and Technology of Silicone, W. Noll, Academic Press Inc. 1998, London, pp 209, 106).

Preferred primary and/or secondary amines, utilizing organic carriers, are those selected from aminoaryl derivatives, polyamines, amino acids and derivatives thereof, substituted amines and amides, glucamines, dendrimers, polyvinylamines and derivatives thereof, and/or copolymer thereof, alkylene polyamine, polyaminoacid and copolymer thereof, cross-linked polyaminoacids, amino substituted polyvinylalcohol, polyoxyethylene bis amine or bis aminoalkyl, aminoalkyl piperazine and derivatives thereof, bis (amino alkyl) alkyl diamine linear or branched, and mixtures thereof.

Preferred aminoaryl derivatives are the amino-benzene derivatives including the alkyl esters of 4-amino benzoate compounds, and more preferably selected from ethyl-4-amino benzoate, phenylethyl-4-aminobenzoate, phenyl-4-aminobenzoate, 4-amino-N'-(3-aminopropyl)-benzamide, and mixtures thereof.

Polyamines suitable for use in the present invention are polyethyleneimine polymers, partially alkylated polyethylene polymers, polyethyleneimine polymers with hydroxyl groups, 1,5-pentanediamine, 1,6-hexanediamine, 1,3 pentanediamine, 3-dimethylpropanediamine, 1,2-cyclohexanediamine, 1,3-bis(aminomethyl)cyclohexane, tripropylenetetraamine, bis (3-aminopropyl)piperazine, dipropylenetriamine, tris(2-aminoethylamine), tetraethylenepentamine, bishexamethylenetriamine, bis(3-aminopropyl) 1,6- hexamethylenediamine, 3,3'-diamino-N-methyldipropylamine, 2-methyl-1,5-pentanediamine, N,N,N',N'-tetra(2-aminoethyl)ethylenediamine, N,N,N',N'-tetra (3-aminopropyl)-1,4-butanediamine, pentaethylhexamine, 1,3-diamino-2-propyl-tert-butylether, isophorondiamine, 4,4'-diaminodicyclohylmethane, N-methyl-N-(3-aminopropyl)ethanolamine, spermine, spermidine, 1-piperazineethaneamine, 2-(bis(2-aminoethyl)amino) ethanol, ethoxylated N-(tallowalkyl)trimethylene diamines, poly[oxy(methyl-1,2-ethanediyl)], α-(2-aminomethylethoxy)-(=C.A.S No. 9046-10-0); poly[oxy(methyl-1,2-ethanediyl)], α-hydro-)-ω-(2-aminomethylethoxy)-, ether with 2-ethyl-2-(hydroxymethyl)-1,3-propanediol (=C.A.S. No. 39423-51-3); commercially available under the tradename Jeffamines T-403, D-230, D-400, D-2000; 2,2',2"-triaminotriethylamine; 2,2'-diamino-diethylamine; 3,3'-diamino-dipropylamine, 1,3 bis aminoethyl-cyclohexane commercially available from Mitsubishi and the C12 Sternamines commercially available from Clariant like the C12 Sternamin(propylenamine)$_n$ with n=¾, and mixtures thereof.

Preferred polyamines are polyethyleneimines commercially available under the tradename Lupasol like Lupasol FG (MW 800), G20wfv (MW 1300), PR8515 (MW 2000), WF (MW 25000), FC (MW 800), G20 (MW 1300), G35 (MW 1200), G100 (MW 2000), HF (MW 25000), P (MW 750000), PS (MW 750000), SK (MW 2000000), SNA (MW 1000000). Of these, the most preferred include Lupasol HF or WF (MW 25000), P (MW 750000), PS (MW 750000), SK (MW 2000000), 620wfv (MW 1300) and PR 1815 (MW 2000), Epomin SP-103, Epomin SP-110, Epomin SP-003, Epomin SP-006, Epomin SP-012, Epomin SP-018, Epomin SP-200, and partially alkoxylated polyethyleneimine, like polyethyleneimine 80% ethoxylated from Aldrich. (Molecular weights are weight averages.)

Preferred amino acids for use herein are selected from tyrosine, tryptophane, lysine, glutamic acid, glutamine, aspartic acid, arginine, asparagine, phenylalanine, proline, serine, histidine, threonine, methionine, and mixture thereof, most preferably selected from tyrosine, tryptophane, and mixture thereof. Preferred amino acid derivatives are selected from tyrosine ethylate, glycine methylate, tryptophane ethylate, and mixtures thereof.

Preferred substituted amines and amides for use herein are selected from nipecotamide, N-coco-1,3-propenediamine; N-oleyl-1,3-propenediamine; N-(tallow alkyl)-1,3-propenediamine; 1,4-diamino cyclohexane; 1,2-diamino-cyclohexane; 1,12-diaminododecane, and mixtures thereof.

Other primary amine compounds suitable for use herein are the glucamines, preferably selected from 2,3,4,5,6-pentamethoxy-glucamine; 6-acetylglucamine, glucamine, and mixture thereof.

Also preferred compounds are the polyethylenimine and/or polypropylenimine dendrimers and the commercially available Starburst® polyamidoamines (PAMAM) dendrimers, generation G0–G10 from Dendritech and the dendrimers Astromols®, generation 1–5 from DSM being DiAminoButane PolyAmine DAB (PA)x dendrimers with $x=2^n\times4$ and n being generally comprised between 0 and 4.

Polyamino acid is one suitable and preferred class of amino-functional polymer. Polyaminoacids are compounds which are made up of amino acids or chemically modified amino acids. They can contain alanine, serine, aspartic acid, arginine, valine, threonine, glutamic acid, leucine, cysteine, histidine, lysine, isoleucine, tyrosine, asparagine, methionine, proline, tryptophan, phenylalanine, glutamine, glycine or mixtures thereof. In chemically modified amino acids, the amine or acidic function of the amino acid has reacted with a chemical reagent. This is often done to protect these chemical amine and acid functions of the amino acid in a subsequent reaction or to give special properties to the amino acids, like improved solubility. Examples of such chemical modifications are benzyloxycarbonyl, aminobutyric acid, butyl ester, pyroglutamic acid. More examples of common modifications of amino acids and small amino acid fragments can be found in the Bachem, 1996, Peptides and Biochemicals Catalog.

Preferred polyamino acid is polylysine. Most preferred are polylysines or polyamino acids where more than about 50% of the amino acids are lysine, since the primary amine function in the side chain of the lysine is the most reactive amine of all amino acids.

The preferred polyamino acid has a (weight) average molecular weight of from about 500 to 10,000,00; more preferably between about 2,000 and 25,000.

The polyamino acid can be cross-linked. The cross-linking can be obtained for example by condensation of the amine group in the side chain of the amino acid like lysine with the carboxyl function on the amino acid or with protein cross linkers like PEG derivatives. The cross-linked polyamino acids still need to have free primary and/or secondary amino groups left for reaction with the unsaturated perfume compound.

The preferred cross-linked polyamino acids have a (weight) average molecular weight of about 20,000 to 10,000,000, more preferably between about 200,000 and 2,000,000.

The polyamino acid or the amino acid can be co-polymerized with other reagents like for instance with acids, amides, acyl chlorides. More specifically with aminocaproic acid, adipic acid, ethylhexanoic acid, caprolactam or mixture thereof. The molar ratio used in these copolymers ranges from about 1:1 (reagent/amino acid (lysine)) to 1:20, more preferably from about 1:1 to 1:10.

The polyamino acid like polylysine can also be partially ethoxylated.

Examples and supply of polyaminoacids containing lysine, arginine, glutamine, asparagine are given in the Bachem 1996, Peptides and Biochemicals catalog.

The polyaminoacid can be obtained before reaction with the active ingredient, under a salt form. For example polylysine can be supplied as polylysine hydrobromide. Polylysine hydrobromide is commercially available from Sigma, Applichem, Bachem and Fluka.

Examples of suitable amino functional polymers containing at least one primary and/or secondary amine group for the purpose of the present invention are:

Polyvinylamine with a MW of about 300-2.10E6;

Polyvinylamine alkoxylated with a MW of about 600, 1200 or 3000 and an ethoxylation degree of 0.5;

Polyvinylamine vinylalcohol-molar ratio 2:1, polyvinylaminevinylformamide-molar ratio 1:2 and polyvinylamine vinylformamide-molar ratio 2:1;

Triethylenetetramine, diethylenetriamine, tetraethylenepentamine;

Bis-aminopropylpiperazine;

Polyamino acid (L-lysine/lauric acid in a molar ratio of 10/1), Polyamino acid (L-lysine/aminocaproic acid/adipic acid in a molar ratio of 5/5/1), ), Polyamino acid (L-lysine/aminocaproic acid/ethylhexanoic acid in a molar ratio of 5/3/1) Polyamino acid (polylysine-cocaprolactam); Polylysine; Polylysine hydrobromide; cross-linked polylysine, amino substituted polyvinylalcohol with a MW ranging from about 400–300,000;

polyoxyethylene bis [amine] available from e.g. Sigma;

polyoxyethylene bis [6-aminohexyl] available from e.g. Sigma;

N,N'-bis-(3-aminopropyl)-1,3-propanediamine linear or branched (TPTA); and 1,4-bis-(3-aminopropyl) piperazine (BNPP).

The more preferred compounds are selected from ethyl-4-amino benzoate, polyethyleneimine polymers commercially available under the tradename Lupasol like Lupasol HF, P, PS, SK, SNA, WF, G20wfv and PR8515; the diaminobutane dendrimers Astramol®, polylysine, cross-linked polylysine, N,N'-bis-(3-aminopropyl)-1,3-propanediamine linear or branched; 1,4-bis-(3-aminopropyl) piperazine, and mixtures thereof. Even most preferred compounds are those selected from ethyl-4-amino benzoate, polyethyleneimine polymers having a molecular weight greater than about 200 daltons including those commercially available under the tradename Lupasol like Lupasol HF, P, PS, SK, SNA, WF, G20wfv and PR8515; polylysine, cross-linked polylysine, N,N'-bis-(3-aminopropyl)-1,3-propanediamine linear or branched, 1,4-bis(-3-aminopropyl) piperazine, and mixtures thereof.

Advantageously, such most preferred primary and/or secondary amine compounds can also provide a fabric appearance benefit, in particular a color appearance benefit, thus providing a resulting amine reaction product which can impart fabric appearance benefits. Further, when the primary and/or secondary amine compound has more than one free primary and/or secondary amine group, several different active ingredients (perfume compounds or other active ingredients) can be linked to the amine compound.

Of course, an excess of the primary and/or secondary amine compound may also be used in the pro-perfume compositions herein as is, i.e. without having been reacted with an unsaturated perfume ester, acid or nitrile perfume ingredient, but with a benefit agent, as described hereinafter, like a perfume composition which is entrapped or embedded within the primary and/or secondary amine compound. Moreover, the primary and/or secondary amine compound may also be reacted with compounds other than the unsaturated perfume esters, acids or nitriles herein, like acyl halides, like acetylchloride, palmytoyl chloride or myristoyl chloride, acid anhydrides like acetic anhydride, alkylhalides or arylhalides to do alkylation or arylation, perfume aldehydes and/or ketones, aldehydes and/or ketones not used as perfume ingredients like formaldehyde, glutaraldehyde, unsaturated ketones, aldehydes or carboxylic acids like 2-decylpropenoic acid, propenal, propenone to form reaction products with the desired physical properties.

Unsaturated Perfume Compound Component

To form the pro-perfume compositions herein, the primary and/or secondary amine compound as described hereinbefore is reacted with a selected type of unsaturated perfume compound. Such a perfume compound has the general structrual formula set forth above and can comprise a number of perfume esters, acids or nitriles. Mixtures or combinations of these types of unsaturated perfume compounds may also be utilized to react with the primary and/or secondary amine compound. These various types of unsaturated perfume compounds are described in greater detail as follows:

A) Unsaturated Perfume Esters

When $R_1$ in the general structural formula set forth hereinbefore is COOR, the perfume compounds which can be reacted with the amine compounds herein are esters. In this instance, R will contain no aldehyde or ketone functionalities and is preferably a $C_{1-20}$ organic moiety. $R_2$ is preferably H, and $R_3$ and $R_4$ are each preferably H or a $C_{1-20}$ organic moiety which may or may not contain aromatic groups or other unsaturation. Most preferably, R is $C_{1-15}$ organic, $R_2$ and $R_3$ are each H, and $R_4$ is H or $C_{1-4}$ alkyl.

Specific unsaturated perfume esters which can be employed in forming the pro-perfume reaction products herein include the crotonates such as 4-me-pentan-2-ol-crotonate, 1-cyclohexyl-et-crotonate (Datilat) and hexylcrotonate; butyl pentenoate; ethyl pentenoate; hexyl angelate; hexyl pentenoate; iso-amyl angelate; iso-butyl angelate; iso-amyl pentenoate; iso-byutul pentenoate; methyl allyl pentenoate; methylgeranate; cis-3-hexenylsalicylate; me-2-nonenoate; 3,7-dimethyl-6-octenyl-2-methylcrotonate; phenylethyl cinnamate; 3,7-dimethyl-2,6-octadienyl-2-methylcrotonate; methyl-2-nonenoate; 4-methyl-pentan-2-ol-crotonate (Frutinat) and 2-cyclopentyl-cyclopentylcrotonate (Pyproprunat). Most preferred are the unsaturated perfume esters which are crotonates, including Datilat, Frutinat and Pyroprunat.

B) Unsaturated Perfume Nitriles

When $R_1$ in the general structural formula set forth hereinbefore is CN, the perfume compounds which can be reacted with the amine compounds herein are nitrites. In this instance, $R_2$ is preferably H or $C_{1-4}$ alkyl, $R_3$ is generally H and $R_4$ is preferably a $C_{1-20}$ organic moiety c ontaining no aldehyde or ketone functionalitites. More preferably, $R_2$ and $R_3$ are each independently H and $R_4$ is $C_{1-10}$ alkyl.

Specific unsaturated perfume nitrites which can be employed in forming the pro-perfume reaction products herein include 3,7-dimethyl-2(3), 6-nonadienenitrile (lemonile), tridecene-2-nitrile, 3,12-tridecadienenitrile, 3-methyl-5-phenyl-2-pentenenitrile, 3,7-dimethyl-2,6-octadienenitrile and cinnamylnitrile. Most preferred are tridecene-2-nitrile, 3,12-tridecadienenitrile, and 3-methyl-5-phenyl-2-pentenenitrile.

C) Unsaturated Perfume Acids

When $R_1$ in the general structural formula set forth hereinbefore is COOH, the perfume compounds which can be reacted with the amine compounds herein are acids. In this instance, $R_2$ is preferably H or $CH_3$, $R_3$ is preferably H and $R_4$ is preferably $C_{1-4}$ alkyl.

Specific unsaturated perfume acids which can be employed in forming the pro-perfume reaction products herein include 2-me-2-pentenoic acid.

Optional Ingredients/Benefit Agents

In addition to the essential unsaturated perfume esters, acids and/or nitrites which are reacted with the amine compund to form the pro-perfumes herein, these pro-perfume compositions can contain a wide variety of optional ingredients. Such optional ingredients can either be reacted with the amine compound as are the essential perfume ingredients or they can be simply physically admixed with and entrapped in the essential pro-perfume components. These optional ingredients are referred to herein as benefit agents since they can provide a beneficial effect on a treated surface, like fabric, upon subsequent contact of the treated surface with water or humidity. Hence, the benefit agent may be selected from a flavor ingredient, a pharmaceutical ingredient, a biocontrol ingredient, an additional perfume composition which may or may not include perfumes which are esters, acids and nitrites, a refreshing cooling ingredient and mixtures thereof.

Typically, the benefit agent can comprise from about 10 to 90%, preferably from about 30 to 85%, more preferably from about 45 to 80% by weight of the pro-perfume component.

Flavor ingredients include spices and flavor enhancers which contribute to the overall flavor perception.

Pharmaceutical ingredients include drugs.

Biocontrol ingredients include biocides, antimicrobials, bactericides, fungicides, algaecides, mildewcides, disinfectants, antiseptics, insecticides, vermicides, and plant growth hormones.

Typical antimicrobials which can be carried by the pro-perfume compositions include amine oxide surfactants, photo-activated bleaches, chlorhexidine diacetate, glutaraldehyde, cinnamon oil and cinnamaldehyde, citric acid, decanoic acid, lactic acid, maleic acid, nonanoic acid, polybiguanide, propylene glycol, cumene sulfonate, eugenol, thymol, benzalkonium chloride, geraniol, and mixtures thereof. Preferred are compounds which can react with the amine compund or the carrier material thereof.

Typical insect and/or moth repellants are perfume ingredients, such as citronellal, citral, N, N diethyl meta toluamide, Rotundial, 8-acetoxycarvotanacetone, and mixtures thereof. Other examples of insect and/or moth repellant for use herein are disclosed in U.S. Pat. Nos. 4,449,987, 4,693,890, 4,696,676, 4,933,371, 5,030,660, 5,196,200, and "Semio Activity of Flavor and Fragrance molecules on various Insect Species", B. D. Mookherjee et al., published in *Bioactive Volatile Compounds from Plants*, ASC Symposium Series 525, R. Teranishi, R. G. Buttery, and H. Sugisawa, 1993, pp. 35–48.

As indicated, the benefit agent may also comprise a perfume composition made of mixture of perfume ingredients including or not the above mentioned esters, acids and/or nitriles. This optional perfume composition can then be entrapped within the pro-perfume component by mixing. Alternatively, such materials may also be reacted with part of the primary and/or secondary amine material. By such means, a more fully complete perfume formulation can then be deposited onto the contacted surface.

Typical of these ingredients include fragrant substances or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders, stabilizers and solvents. These auxiliaries are also included within the meaning of "perfume", as used herein. Typically, perfumes are complex mixtures of a plurality of organic compounds.

Suitable perfumes are disclosed in U.S. Pat. Nos. 5,500, 138 and 4, 853,369 and WO 96/12785, said patent publications being incorporated herein by reference.

Examples of such preferred optional perfume components are those having a low Odor Detection Threshhold and are selected from: 2-methyl-2-(para-iso-propylphenyl)-propionaldehyde, 1-(2,6,6-trimethyl-2-cyclohexan-1-yl)-2-buten-1-one and/or para-methoxy-acetophenone. Even more preferred are the following compounds: undecylenic aldehyde, undecalactone gamma, heliotropin, dodecalactone gamma, p-anisic aldehyde, para hydroxy-phenyl-butanone, cymal, benzyl acetone, ionone alpha, p.t.bucinal, damascenone, ionone beta, methyl-nonyl ketone, methyl heptine carbonate, linalool, indol, cis-3-hexenyl salicylate, vanillin, methyl isobutenyl tetrahydropyran, ethylvanillin, coumarin, ethyl methyl phenyl glycidate, eugenol, methylanthranilate, iso eugenol, beta naphtol methyl ester, herbavert, lyral, allyl amyl glycolate, dihydro iso jasmonate, ethyl-2-methylbutyrate, nerol, and phenylacetaldehyde. Most preferably the optional perfume ingredients comprise at least about 5%, more preferably at least about 10% of the pro-perfume compositions herein.

Generally the preferred optional perfumes are those perfume compositions comprising at least about 10%, preferably about 25%, by weight of perfume ingredient with a ClogP of at least about 2.0, preferably of at least about 3.0 and boiling point of at least about 250° C. More preferred optionals and those compositions comprising at least about 20%, preferably about 35%, by weight of perfume ingredient with a ClogP at least about 2.0, more preferably of at least about 3.0, and boiling point of less than or equal to about 250° C.

Pro-Perfume Composition Preparation

The pro-perfume compositions herein can be prepared by simply admixing the amine compound and the essential unsaturated perfume esters, acids and/or nitrites under conditions which are sufficient to bring about the Michael Addition reaction of these components. Frequently this admixing is carried out using high shear agitation. Temperatures of from about 10° C. to 80° C. may be utilized. Additional benefit agents may also be added to the reaction mixture. The reaction mechanism involving the reaction of the amine compound with the ester, acid or nitrile perfume compounds is described in greater detail in *Introduction to Organic Chemistry*: A. Streitwieser Jr., C. H. Heathcock; McMillan Publishing Co., New York, 1985, which publication is incorporated herein by reference.

Typically equimolar amount of the reactants can be employed. On a weight basis, reactant amounts can vary widely, ranging from about 5:1 to 1:5 for the two essential components. (amine compound and unsaturated perfume compounds). To form a suitable reaction medium, the reactants may also be admixed with one or more components of the cleaning or fabric treatment products into which the pro-perfume compositions herein will eventually be formulated.

As indicated, the resulting pro-perfume reaction products are relatively viscous materials. Frequently the viscosity of the amine compound reaction products will be greater than about 1000 cPs, more preferably greater than about 500,000 cPs, and even more preferably greater than about 1,000,000 cPs.

Large scale production of the pro-perfume reaction products of this invention can be carried out in a manner analogous to the preparation of the pro-perfumes as described in WO 01/04084, WO 01/04247 and WO 01/04248, all published Jan. 18, 2001.

Substrate Treatment Products

The pro-perfume compositions herein can be incorporated into a wide variety of substrate-treating products. Substrates treated by such products can include fabrics, hard surfaces, hair, skin, teeth, paper, diapers, and the like. The substrate-treating products herein will generally comprise from about 0.001% to 10% by weight of the pro-perfume materials.

Preferred is incorporation of the pro-perfume compositions of the present invention into a wide variety of cleaning products and fabric treatment products. Such products include both laundry and cleaning compositions which are typically used for laundering fabrics and cleaning hard surfaces such as dishware, floors, bathrooms, toilet, kitchen and other surfaces in need of a delayed release of perfume ketone and aldehyde. Accordingly, by laundry and cleaning compositions, these are to be understood to include not only detergent compositions which provide fabric cleaning benefits, but also compositions such as hard surface cleaning which provide hard surface cleaning benefit.

Products in which the pro-perfumes herein can be incorporated also include fabric treatment products such as fabric softeners or conditioners. Such products do not necessarily impart a cleaning benefit to fabrics treated therewith.

Preferred as products in which the pro-perfumes herein can be incorporated are are those laundry and fabric treatment, e.g., softener, compositions which result in contacting of the pro-perfume with fabric.

The effectiveness of the delivery to treated surfaces of the pro-perfumes herein can be quantified by means of a parameter called the Dry Surface Odor Index. Such a parameter is fully described in PCT Application No. WO 00/02982, which publication is incorporated by reference herein. Preferably, the pro-perfume compositions herein which are incorporated into cleaning and fabric treatment products will provide a Dry Surface Odor Index of more than about 5 and preferably at least about 10.

In general, the pro-perfume compositions herein can be incorporated into cleaning or fabric treatment products herein at levels which range from about 0.005% to 5% by weight, more preferably from about 0.02% to 0.5% by weight. For cleaning products, the pro-perfume will generally be incorporated at concentrations of from about 0.005% to 2% by weight, along with from about 1% to 50% by weight of a detersive surfactant. For fabric treatment products, the pro-perfume will generally be incorporated at concentrations of from about 0.005% to 5% by weight, along with from about 1% to 50% by weight of a fabric softening or treating agent. The cleaning and fabric treatment products containing the pro-perfumes herein can comprise a wide variety of additional adjuvants which are conventional for use in products of these types. Extensive disclosure of such conventional adjuvants can be found in PCT Patent Application Nos. WO 00/02982 and WO 00/02987, which publications are incorporated herein by reference.

The cleaning and treatment products which contain the pro-perfumes herein may take a variety of physical forms including liquids, gels or foams in aqueous or nonaquous form, granular form or tablet form. An especially preferred form for products of this type is a liquid detergent composition, e.g., a heavy duty liquid (HDL) detergent for fabric laundering. The pro-perfume can be processed into liquid detergents via a silicone dispersion, for example by dispersing the pro-perfume into dimethicone silicone in about a 1:1 weight ratio, in the manner described in WO 01/51599, published Jul. 19, 2001.

Substrate Treatment with Pro-Perfumes

In its use aspects, the present invention provides a method for imparting a sustained, long-lasting slow fragrance release feature to various types of substrates. In such a method, the substrate to be treated, such as fabric or a hard surface, is contacted in conventional manner with an aqueous solution or dispersion which contains from about 0.001% to 10%, more preferably from about 0.01 % to 5%, by weight of the pro-perfume reaction products of this invention.

Such aqueous solutions can be formed, for example, by dissolving or diluting a substrate-treating product of the type hereinbefore described in or with water in the context of normal usage of such products. Thus, for example, fabrics or hard surfaces may be treated with aqueous dispersions of the pro-perfumes herein in the context of normal laundering, cleaning or fabric treatment operations using laundry, hard surface cleaner or fabric softening products which contain the pro-perfumes therein.

During the course of such operations, the pro-perfume composition is deposited on the substrate surface where it remains after the substrate-treating operation is complete. The substrate is then generally dried in conventional manner, with the pro-perfume composition remaining on the dried substrate surface until after the drying operation is complete. Thereafter, over time, the weakly chemically bound perfume component of the pro-perfume composition is released from its amine backbone, thereby providing sustained-release fragrance and odor characteristics to the substrates which have been treated in accordance with the method herein.

Preparation of the pro-perfumes herein and their incorporation into certain types of substrate-treating, e.g., cleaning products, can be illustrated by the following examples:

EXAMPLE I

A pro-perfume composition is prepared which comprises the reaction product of the polyethyleneimine Lupasol WF (MW=25,000) with a Datilat unsaturated ester perfume compound. To prepare such a pro-perfume, 60 grams of Datilat are mixed with Luposol (40 grams) in a vessel for 30 minutes. This mixture is then left for 7 hours at 60° C. After this time, it is demonstrated by NMR analysis that 65% of the Datilat has been reacted with the Lupasol to form Michael adducts. The resulting reaction product can be added as a pro-perfume composition to a wide variety of cleaning and fabric treament product types.

EXAMPLE II

A pro-perfume composition is prepared which comprises the reaction product of the polyethyleneimine Lupasol G20 (MW=1300) with a Datilat unsaturated ester perfume compound. In a similar manner to that set forth in Example I, 60 grams of Datilat are mixed with 40 grams of the Lupasol in a vessel for 30 minutes and left for 7 hours at 60° C. Again, it is demonstrated with NMR that 65% of the Datilal is reacted with the Lupasol to form Michael adducts.

This new compound is then further processed into a powder form by mixing 20 g of the reaction compound in 80 g of TAE80 nonionic surfactant at 70° C. until a homogeneous dispersion is obtained. The mixing is done with a high force mixer (Ultra Turrax) for two minutes. The reaction product/TAE80 dispersion is then further poured onto 200 g of dry fine carbonate, and mixed in a food processor to obtain solid particles. The resulting solid particles can be added as such to the detergent product.

EXAMPLE III

C12 Sternamine(propyleneamine)n with n=3 is reacted with pyroprunat using methanol as a solvent. Approximately 4.7 g of C12 Sternamine(propyleneamine)3 are put together with 5.3 g pyroprunat in methanol and solvent and stirred for 48 hours under reflux. Then the solvent is removed.NMR demonstrates that 76% of the pyroprunat has reacted with the C12 sternamine(propyleneamine)3 compound. Substantially similar results are obtained when frutinat is substituted for pyroprunat in this procedure.

A variety of detergent compositions are prepared having the compositions shown in the following Examples IV through XI. In these examples the abbreviated component identifications have the following meanings:

| | |
|---|---|
| Dispersant: | Ethoxylated tetraethylenepentamine |
| LAS: | Sodium linear $C_{12}$ alkyl benzene sulphonate |
| CFAA: | $C_{12}$–$C_{14}$ alkyl N-methyl glucamide |
| HEDP: | Hydroxyethane dimethylene phosphonic acid |
| DETPMP: | Diethylene triamine penta (methylene phosphonic acid), marketed by Monsanto under the Tradename Dequest 2060 |

-continued

| | |
|---|---|
| TEPAE | Tetreaethylenepentaamine ethoxylate |
| PVP | Polyvinylpyrrolidone polymer |
| PVNO | Polyvinylpyridine-N-Oxide, with an average molecular weight of 50,000. |
| Brightener | Disodium 4,4'-bis(2-sulphostyryl)biphenyl and/or Disodium 4,4'-bis(4-anilino-6-morpholino-1.3.5-triazin-2-yl) stilbene-2:2'-disulfonate. |
| Suds Suppressor | 25% paraffin wax Mpt 50° C., 17% hydrophobic silica, 58% paraffin oil Granular suds suppressors 12% Silicone/silica, 18% stearyl alcohol, 70% starch in granular form |
| Enzymes: | Protease, amylase, cellulase and/or lipase |
| SRP | Anionically end capped polyesters. |
| MEA | Monoethanolamine |
| SCS | Sodium Cumene Sulfonate |
| Alkoxylated alcohol: | Tallow alcohol ethylene oxide condensate of type tallow alcohol, condensed with an average of from 50 to 100 moles of ethylene oxide |
| CFAA: | $C_{12}$–$C_{14}$ (coco) alkyl N-methyl glucamide |
| CxyAS: | Sodium $C_{1x}$–$C_{1y}$ alkyl sulphate |
| CxyEz: | $C_{1x}$–$C_{1y}$ predominantly linear primary alcohol condensed with an average of z moles of ethylene oxide |
| CxyEzS: | Sodium $C_{1x}$–$C_{1y}$ alkyl sulfate condensed with z moles of ethylene oxide |
| FAS: | Fatty alkyl sulfate |
| LAS: | Sodium linear $C_{11}$–$C_{13}$ alkyl benzene sulfonate |
| QAS(1): | $R_2.N^+(CH_3)_2(C_2H_4OH)$, wherein $R_2 = C_{12}$–$C_{14}$ |
| QAS(2): | $R_2.N^+(CH_3)_2(C_2H_4OH)$, wherein $R_2 = C_8$–$C_{11}$ |
| Carbonate: | Anhydrous sodium carbonate |
| Silicate: | Amorphous sodium silicate ($SiO_2$:$Na_2O$ = from 2:1 to 4:1) |
| Sulfate: | Anhydrous sodium sulfate |
| Citric acid: | Anhydrous citric acid |
| NaSKS-6: | Crystalline layered silicate of formula d-$Na_2Si_2O_5$ |
| STPP: | Anhydrous sodium tripolyphosphate |
| Zeolite A: | Hydrated sodium aluminosilicate of formula $Na_{12}(AlO_2SiO_2)_{12}$.27H2O having a primary particle size in the range of from 0.1 to 10 micrometers (weight expressed on an anhydrous basis) |
| DTPA: | Diethylene triamine pentaacetic acid |
| EDDS: | Ethylenediamine-N'N'-disuccinic acid, (S,S) isomer in the form of a sodium salt |
| HEDP: | 1,1-hydroxyethane diphosphonic acid |
| Mg sulfate: | Anhydrous magnesium sulfate |
| PB1: | Anhydrous sodium perborate bleach of nominal formula $NaBO_3.H_2O$ |
| PB4: | Sodium perborate tetrahydrate of nominal formula $NaBO_3.4H_2O$ |
| Percarbonate: | Sodium percarbonate of the nominal formula $2Na_2CO_3.3H_2O_2$ |
| NOBS: | Nonanoyloxybenzene sulfonate |
| TAED: | Tetraacetylethylenediamine |
| Photobleach(1): | Sulfonated zinc phthalocyanine |
| EMC: | Ester modified cellulose |
| PEO: | Polyethylene oxide having a weight average molecular weight of from 100000 to 1000000 |
| Clay: | Smectite clay |
| PEG: | Polyethylene glycol having a weight average molecular weight of x, wherein X = from 1000 to 12000 |
| CMC: | Sodium carboxymethyl cellulose |
| MA/AA(1): | Copolymer of maleic/acrylic acid, having a weight average molecular weight of from 50000 to 90000, wherein the ratio of maleic to acrylic acid is from 1:3 to 1:4 |
| QEA(1): | bis(($C_2H_5O$)($C_2H_4O$)n)($CH_3$)-N+-$C_xH_{2x}$-N+-($CH_3$)-bis(($C_2H_5O$)($C_2H_4O$)n), wherein n = from 20 to 30, and x = from 3 to 8 |
| QEA(2): | sulphonated or sulphated bis(($C_2H_5O$)($C_2H_4O$)n)($CH_3$)-N+-$C_xH_{2x}$-N+-($CH_3$)-bis(($C_2H_5O$)($C_2H_4O$)n), wherein n = from 20 to 30, and x = from 3 to 8 |
| SRP(1): | Anionically end capped polyesters |
| Silicone antifoam: | Polydimethyl siloxane foam controller with siloxane-oxyalkylene copolymer as dispersing agent, wherein the ratio of said foam controller to said dispersing agent is from 10:1 to 100:1 |

-continued

| | |
|---|---|
| Soap: | Sodium linear alkyl carboxylate which is derived from a mixture of tallow and coconut fatty acids, wherein the weight ratio of tallow to coco fatty acids is 80/20 |

EXAMPLE IV

Liquid Detergent Composition

A heavy duty liquid (HDL) detergent composition is prepared containing the pro-perfume composition of Example I. Such a liquid detergent composition has the following formula:

| Component | Wt. % |
|---|---|
| $C_{12-15}$ alkyl ether (2.5) sulfate | 19.0 |
| $C_{12-13}$ alkyl ethoxylate (9.0) | 2.00 |
| $C_{12-14}$ glucose amide | 3.50 |
| Citric Acid | 3.00 |
| $C_{12-14}$ Fatty Acid | 2.00 |
| MEA | to pH 8 |
| Ethanol | 3.41 |
| Propanediol | 6.51 |
| Borax | 2.5 |
| Dispersant | 1.18 |
| Na Toluene Sulfonate | 2.50 |
| Pro-Perfume Composition* of Example I | 0.3% |
| Dye, Brighteners, Enzymes, Preservatives, Suds Suppressor, Other Minors, Water | Balance 100% |

*Including the Neodol

EXAMPLE V

The following liquid detergent formulations are prepared according to the present invention:

| | A | B | C | D | E |
|---|---|---|---|---|---|
| LAS | 11.5 | 9.0 | — | 4.0 | — |
| C25E2.5S | — | 3.0 | 18.0 | — | 16.0 |
| C45E2.25S | 11.5 | 3.0 | — | 16.0 | — |
| C23E9 | — | 3.0 | 2.0 | 2.0 | 1.0 |
| C23E7 | 3.2 | — | — | — | — |
| CFAA | — | — | 5.0 | — | 3.0 |
| TopPalmKernel Fatty Acid | 2.0 | — | 2.0 | 0.5 | 2.0 |
| Citric (50%) | 6.5 | 1.0 | 2.5 | 4.0 | 2.5 |
| Ca and/or Ca formate | 0.6 | 0.7 | 0.2 | 0.05 | 0.05 |
| SCS | 4.0 | 1.0 | 3.0 | 1.2 | — |
| Borate | 0.6 | — | 3.0 | 2.0 | 3.0 |
| Na hydroxide | 6.0 | 2.0 | 3.5 | 4.0 | 3.0 |
| Ethanol | 2.0 | 1.0 | 4.0 | 4.0 | 3.0 |
| 1,2 Propanediol | 3.0 | 2.0 | 8.0 | 8.0 | 5.0 |
| Monoethanolamine | 3.0 | 1.5 | 1.0 | 2.5 | 1.0 |
| TEPAE | 2.0 | — | 1.0 | 1.0 | 1.0 |
| Pro-Perfume of Ex. III | 0.1 | 0.02 | 0.1 | 0.01 | 0.05 |
| Enzymes | 0.03 | 0.01 | 0.03 | 0.02 | 0.02 |
| SRP | 0.2 | — | 0.1 | — | — |
| DTPA | — | — | 0.3 | — | — |
| PVNO | — | — | 0.3 | — | 0.2 |
| Brightener | 0.2 | 0.07 | 0.1 | — | — |
| Suds suppressor | 0.04 | 0.02 | 0.1 | 0.1 | 0.1 |
| Miscellaneous and water | Balance to 100% | | | | |

EXAMPLE VI

Heavy duty liquid fabric cleaning compositions in accordance with the invention are prepared as follows:

| | A | B |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Pro-Perfume (Ex. I) | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

EXAMPLE VII

Heavy-duty liquid fabric cleaning compositions in accordance with the invention are prepared as follows:

| | A | B | C |
|---|---|---|---|
| C25AES | 18.0 | 15.0 | 14.0 |
| LAS | 5.8 | 5.0 | 4.0 |
| $C_{8-10}$ Amine | 1.4 | 2.0 | — |
| Nonionic 24-7 | 2.8 | 2.0 | 3.0 |
| Citric acid | 2.5 | 3.0 | 3.0 |
| Fatty acid | 8.5 | 3.0 | 3.0 |
| Enzymes | 0.02 | 0.02 | 0.006 |
| Boric acid | 2.0 | 2.0 | 2.0 |
| Ethoxylate tetraethylene pentaimine | 0.9 | 1.0 | 1.0 |
| Polyethylene imine ethoxylated | 0.7 | — | 1.0 |
| DETPMP | 0.3 | — | — |
| HEDP | 0.35 | — | — |
| Ethanol | 1.0 | 3.0 | 3.0 |
| 1,2,propanediol | 8.0 | 4.0 | 5.0 |
| MEA | 9.8 | 2.0 | 2.0 |
| Na Cumene Sulfonate | 2.0 | — | — |
| Suds suppressors | 0.25 | 0.01 | 0.01 |
| Pro-Perfume of Example III | 0.07 | 0.03 | 0.01 |
| Minors (Other perfumes, brighteners, . . . ) and water | Up to 100% | | |

EXAMPLE VIII

Granular Detergent Composition

A heavy duty granular detergent (HDG) composition is prepared containing the pro-perfume composition of Example I. Such a granular detergent composition has the following formula:

| Component | Wt. % |
|---|---|
| $C_{12}$ Linear alkyl benzene sulfonate | 9.31 |
| $C_{14-15}$ alkyl sulfonate | 12.74 |
| Zeolite Builder | 27.79 |
| Sodium Carbonate | 27.31 |
| PEG 4000 | 1.60 |
| Dispersant | 2.26 |
| $C_{12-13}$ alkyl ethoxylate (E9) | 1.5 |
| Sodium Perborate | 1.03 |
| Soil Release Polymer | 0.41 |
| Enzymes | 0.59 |
| Pro-Perfume of Example II | 0.15 |
| Brightener, Suds Suppressor, Other Minors, Moisture, Sulfate | Balance |
| | 100% |

EXAMPLE IX

Low Sudsing Granular Detergent Composition

A relatively low-sudsing, heavy duty granular detergent (HDG) composition is prepared containing the pro-perfume composition of Example III. Such a granular detergent composition has the following formula:

| Component | Wt. % |
|---|---|
| $C_{12}$ Linear alkyl benzene sulfonate | 8.0 |
| C28AS | 6.0 |
| C25E3S | 1.0 |
| CFAA | 1.0 |
| Zeolite Builder | 22.0 |
| Sodium Carbonate | 12.0 |
| QAS(2) | 1.2 |
| Alkoxylated Alcohol | 0.4 |
| $C_{12-18}$ alkyl ethoxylate (E5) | 3.5 |
| Sodium Percarbonate | 12.0 |
| NOBS | 0.2 |
| TAED | 5.0 |
| Soil Release Polymer | 0.2 |
| Citric Acid | 1.5 |
| Enzymes | 0.4 |
| Pro-Perfume of Example II | 0.5 |
| Sodium Sulfate | 3.0 |
| Silicate | 0.6 |
| NaSKS-6 | 8.0 |
| EDDS | 0.4 |
| HEDP | 0.5 |
| MgSulfate | 0.15 |
| CMC | 0.4 |
| MA/AA(1) | 1.0 |
| QEA(1) | 1.1 |
| Silicone Antifoam | 0.3 |
| Brightener, Other Minors, Moisture, | Balance |
| | 100% |

EXAMPLE X

Phosphate-Based Granular Detergent Composition

A relatively low-sudsing, phosphate-built,heavy duty granular detergent (HDG) composition is prepared containing the pro-perfume composition of Example II. Such a granular detergent composition has the following formula:

| Component | Wt. % |
|---|---|
| $C_{12}$ Linear alkyl benzene sulfonate | 6.0 |
| C25E3S | 1.0 |
| STPP | 1.0 |
| Zeolite A | 0.5 |
| Sodium Carbonate | 15.0 |
| QAS(1) | 0.5 |
| Alkoxylated Alcohol | 0.5 |
| $C_{14-15}$ alkyl ethoxylate (E7) | 5.0 |
| PB1 | 6.0 |
| PB4 | 4.0 |
| TAED | 1.5 |
| Photobleach (1) | 0.005 |
| Citric Acid | 1.2 |

-continued

| Component | Wt. % |
|---|---|
| Enzymes | 0.76 |
| Pro-Perfume of Example II | 1.4 |
| Sodium Sulfate | 24.0 |
| Silicate | 3.0 |
| EMC | 0.5 |
| DTPA | 0.4 |
| SRP(1) | 0.1 |
| MgSulfate | 1.4 |
| CMC | 0.05 |
| MA/AA(1) | 2.0 |
| QEA(1) | 5.0 |
| Silicone Antifoam | 0.2 |
| Brightener, Other Minors, Moisture, | Balance 100% |

EXAMPLE XI

Fabric Softening Granular Detergent Composition

A heavy duty granular detergent (HDG) composition which provides through-the-wash fabric softening is prepared containing the pro-perfume composition of Example I. Such a granular detergent composition has the following formula:

| Component | Wt. % |
|---|---|
| $C_{12}$ Linear alkyl benzene sulfonate | 7.0 |
| FAS | 1.0 |
| Zeolite A | 14.0 |
| Sodium Carbonate | 33.0 |
| QAS(2) | 1.2 |
| Alkoxylated Alcohol | 0.06 |
| $C_{12-18}$ alkyl ethoxylate (E5) | 2.5 |
| Sodium Percarbonate | 10.0 |
| DTPA | 0.3 |
| TAED | 2.4 |
| PEO | 0.2 |
| Clay | 9.0 |
| Enzymes | 0.4 |
| Pro-Perfume of Example II | 0.83 |
| Sodium Sulfate | 12.0 |
| Silicate | 1.5 |
| EDDS | 0.08 |
| HEDP | 0.1 |
| MgSulfate | 0.5 |
| MA/AA(1) | 0.3 |
| EMC | 1.2 |
| Soap | 0.6 |
| Silicone Antifoam | 0.05 |
| Brightener, Other Minors, Moisture, | Balance 100% |

What is claimed is:

1. A pro-perfume composition suitable for incorporation into cleaning or fabric treatment products, which composition comprises the reaction product of a primary and/or secondary amine compound with an unsaturated perfume compound of the formula:

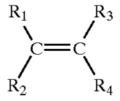

wherein $R_1$ is CN, COOH or COOR, with R being an organic moiety containing no aldehyde or ketone functionalities; and $R_2$, $R_3$ and $R_4$ each independently being organic moieties which, together with $R_1$, render the resulting compound a material having perfume characteristics; and wherein said amine compound is selected so as to provide the resulting reaction product in the form of a viscous fluid having a viscosity ranging from about 500 to 100,000,000 centipoise.

2. A pro-perfume composition according to claim 1 wherein said amine compound is one having an Odor Intensity Index or less than that of a 1% solution of methylanthranilate in dipropylene glycol.

3. A pro-perfume composition according to claim 2 wherein $R_1$ is COOR with R being a $C_{1-20}$ organic moiety; $R_2$ and $R_3$ are each independently H or $C_{1-4}$ alkyl with at least one of $R_2$ and $R_3$ being H, and $R_4$ is H or a $C_{1-20}$ organic moiety.

4. A composition according to claim 3 wherein the amine compound is selected from ethyl-4-amino benzoate, polyethyleneimine polymers; diaminobutane dendrimers, polylysine, cross-linked polylysine, linear or branched N,N'-bis-(3-aminopropyl)-1,3-propanediamine; 1,4-bis-(3-aminopropyl) piperazine, and mixtures thereof.

5. A composition according to claim 4 wherein said perfume compound is an ester perfume compound having an unsaturated double bond in conjugation with an electron withdrawing group.

6. A pro-perfume composition according to claim 5 wherein said amine compound is selected from a polyethyleneimine polymor.

7. A pro-perfume composition according to claim 4 wherein said unsaturated perfume compound is an ester perfume compound selected from 4-me-pentan-2-ol-crotonate, 1-cyclohexyl-et-crotonate (Datilat); hexylcrotonate; butyl pentenoate; ethyl pentenoate; hexyl angelate; hexyl pentenoate; iso-amyl angelate; iso-butyl angelate; iso-amyl pentenoate; iso-byutul pentenoate; methyl allyl pentenoate; methylgeranate; cis-3-hexenylsalicylate; me-2-nonenoate; 3,7-dimethyl-6-octenyl-2-methylcrotonate; phenylethyl cinnamate; 3,7-dimethyl-2,6-octadienyl-2-methylcrotonate; methyl-2-nonenoate; 4-methyl-pentan-2-ol-crotonate (Frutinat) and 2-cyclopentyl-cyclopentylcrotonate (Pyproprunat).

8. A pro-perfume composition suitable for incorporation into cleaning or fabric treatment products, which composition comprises the Michael Addition reaction product of A) an amine compound selected from polyethyleneimines having a molecular weight greater than about 200 daltons, amine-derivatized silicones and polylysine; with B) an ester perfume compound having an unsaturated double bond in conjugation with an electron withdrawing group;

said reaction product being in the form of a viscous fluid having a viscosity ranging from about 5,000 to 15,000,000 centipoise.

9. A pro-perfume composition suitable for incorporation into cleaning or fabric treatment products, which composition comprises the Michael Addition reaction product of:

A) an amine compound selected from polyethyleneimines having a molecular weight greater than about 200 daltons, amine-derivatized silicones and polylysine; with B) a perfume compound selected from 4-me-pentan-2-ol-crotonate, 1-cyclohexyl-et-crotonate (Datilat); hexylcrotonate; butyl pentenoate; ethyl pentenoate; hexyl angelate; hexyl pentenoate; iso-amyl angelate; iso-butyl angelate; iso-amyl pentenoate; iso-butyl pentenoate; methyl allyl pentenoate; methylgeranate; cis-3-hexenylsalicylate; me-2-nonenoate; 3,7-dimethyl-6-octenyl-2-methylcrotonate; phenylethyl cinnamate; 3,7-dimethyl-2,6-octadienyl-2-methylcrotonate; methyl-2-nonenoate; 4-methyl-pentan-2-ol-crotonate (Frutinat); 2-cyclopentyl-cyclopentylcrotonate (Pyproprunat); 3,7-dimethyl-2(3), 6-nonadienenitrile (lemonile); tridecene-2-nitrile; 3,12-tridecadienenitrile; 3-methyl-5-phenyl-2-pentenenitrile; 3,7-dimethyl-2,6-octadienenitrile; cinnamylnitrile; and 2-me-2-pentenoic acid.

10. A composition according to claim 9 wherein the pro-perfume composition further comprises an additional perfume composition.

11. A substrate-treating composition comprising a substrate treating agent and from about 0.001% to 10% by weight of a pro-perfume composition according to claim 1.

12. A cleaning composition comprising from about 1% to 50% by weight of a detersive surfactant and from about 0.005% to 2% by weight of a pro-perfume composition according to claim 1.

13. A cleaning composition comprising from about 1% to 50% by weight of a detersive surfactant and from about 0.005% to 2% by weight of a pro-perfume composition according to claim 8.

14. A cleaning composition according to claim 13 which is in the form of a liquid detergent composition.

15. A fabric treatment composition comprising from about 1% to 50% by weight of a fabric softening or treatment agent and from about 0.005% to 5% of a pro-perfume composition according to claim 1.

16. A fabric treatment composition comprising from about 1% to 50% by weight of a fabric softening or treatment agent and from about 0.005% to 5% of a pro-perfume composition according to claim 8.

17. A method for treating substrates to impart thereto surface substantive, slow odor release perfume materials, which method comprises contacting a substrate with an aqueous solution containing from about 0.001% to 10% by weight of a pro-perfume composition according to claim 1; and thereafter drying said fabric or hard surface substrate in a manner which leaves said pro-perfume composition deposited on said substrate.

18. A method for treating substrates to impart thereto surface substantive, slow odor release perfume materials, which method comprises contacting a substrate with an aqueous solution containing from about 0.001% to 10% by weight of a pro-perfume composition according to claim 8; and thereafter drying said fabric or hard surface substrate in a manner which leaves said pro-perfume composition deposited on said substrate.

19. A method according to claim 18 wherein said substrate is a fabric or hard surface.

* * * * *